(12) United States Patent
Matsui et al.

(10) Patent No.: US 10,894,088 B2
(45) Date of Patent: Jan. 19, 2021

(54) BSH COMPLEX FOR BORON NEUTRON CAPTURE THERAPY

(71) Applicant: National University Corporation Okayama University, Okayama (JP)

(72) Inventors: Hideki Matsui, Okayama (JP); Shuichi Furuya, Okayama (JP); Hiroyuki Michiue, Okayama (JP); Hiroki Kakuta, Okayama (JP); Yasuaki Takeuchi, Okayama (JP)

(73) Assignee: National University Corporation Okayama University, Okayama (JP)

( * ) Notice: Subject to any disclaimer, the term of this patent is extended or adjusted under 35 U.S.C. 154(b) by 0 days.

(21) Appl. No.: 16/463,747

(22) PCT Filed: Nov. 24, 2017

(86) PCT No.: PCT/JP2017/043220
§ 371 (c)(1),
(2) Date: May 23, 2019

(87) PCT Pub. No.: WO2018/097335
PCT Pub. Date: May 31, 2018

(65) Prior Publication Data
US 2020/0121800 A1    Apr. 23, 2020

(30) Foreign Application Priority Data

Nov. 25, 2016  (JP) .................................. 2016-229302

(51) Int. Cl.
| | |
|---|---|
| *A61K 38/00* | (2006.01) |
| *A61K 47/64* | (2017.01) |
| *A61K 47/69* | (2017.01) |
| *A61P 35/00* | (2006.01) |
| *A61K 9/00* | (2006.01) |
| *A61K 33/22* | (2006.01) |

(52) U.S. Cl.
CPC ............ *A61K 47/64* (2017.08); *A61K 9/0019* (2013.01); *A61K 33/22* (2013.01); *A61K 47/6941* (2017.08); *A61P 35/00* (2018.01)

(58) Field of Classification Search
None
See application file for complete search history.

(56) References Cited

U.S. PATENT DOCUMENTS

2008/0312130 A1* 12/2008 Kaneda ................. A61K 47/60
514/1.1

FOREIGN PATENT DOCUMENTS

| EP | 2319850 A1 | 5/2011 |
|---|---|---|
| JP | 2013-87098 A | 5/2013 |

OTHER PUBLICATIONS

European search report (EESR) dated Jun. 30, 2020 in the corresponding European Patent Application No. 17873605.4.
Maruyama K et al., "Intracellular targeting of sodium mercaptoundecahydrododecarborate (BSH) to solid tumors by transferrin-PEG liposomes, for boron neutron-capture therapy (BNCT)", Journal of Controlled Release, vol. 98, No. 2, Aug. 11, 2004 (Aug. 11, 2004), pp. 195-207.
Sadaaki Kimura et al., "Synthesis and evaluation of cyclic RGD-boron cluster conjugates to develop tumor-selective boron carriers for boron neutron capture therapy", Bioorganic & Medicinal Chemistry: A Tetrahedron Publication for the Rapid Dissemination of Full Origianal Research Papers and Critical Reviews on Biomolecular Chemistry, Medicinal Chemistry and Related Disciplines, vol. 19, No. 5, Jan. 12, 2011, pp. 1721-1728.
Christina Karavasili et al., "Bioactive Self-Assembling Lipid-Like Peptides as Permeation Enhancers for Oral Drug Delivery", Journal of Pharmaceutical Sciences, vol. 104, No. 7, Jul. 2015, pp. 2304-2311.
Daizo Yoshida et al., "A transfection method for short interfering RNA with the lipid-like self-assembling nanotube, A6K", Medical Molecular Morphology, vol. 46. No. 2, Feb. 5, 2013, pp. 86-91.
Jing Wang et al., "Dynamic self-assembly of surfactant-like peptides A6K and A9K", Soft Matter, vol. 5, No. 20, 2009, p. 3870.
International Search Report dated Jan. 16, 2018 in PCT/JP2017/043220, 2 pages.
International Preliminary Report on Patentability dated Sep. 6, 2018 in PCT/JP2017/043220 (submitting English translation only), 9 pages.
Nakmura, H., et al., "Historical development and current status of boron delivery agents for boron neutron capture therapy", Radio-isotopes, 2015, vol. 64, No. 1, pp. 47-58 (with English abstract).
Chen, Y., et al., "Self-assembling surfactant-like peptide $A_6K$ as potential delivery system for hydrophobic drugs", International Journal of Nanomedicine, vol. 10, 2015, pp. 847-858.
Fatouros, D.G., et al., "Lipid-like Self Assembling Peptide Nanovesicles for Drug Delivery", ACS, Applied Materials & Interfaces, vol. 6 issue 11, May 12, 2014, pp. 8184-8189.

(Continued)

*Primary Examiner* — Jeanette M Lieb
(74) *Attorney, Agent, or Firm* — Oblon, McClelland, Maier & Neustadt, L.L.P.

(57) ABSTRACT

The present invention provides: a complex of a mercaptoundecahydrodecaborate (BSH) and a peptide, the complex for boron neutron capture therapy (BNCT); a method for producing the complex; and a cancer therapy using the complex.

10 Claims, 8 Drawing Sheets
(2 of 8 Drawing Sheet(s) Filed in Color)
Specification includes a Sequence Listing.

(56) References Cited

OTHER PUBLICATIONS

Michiue, H., et al., "The acceleration of boron neutron capture therapy using multi-linked mercaptoundecahydrododecaborate (BSH) fused cell-penetrating peptide", Biomaterials, vol. 35 issue 10, Mar. 2014, pp. 3396-3405.

Iguchi, Y., et al., "Tumor-specific delivery of BSH-3R for boron neutron capture therapy and postition emission tomography imaging in a mouse brain tumor model", Biomaterials, vol. 56, Jul. 2015, pp. 10-17.

* cited by examiner

SEQUENCE LISTING

```
<160> NUMBER OF SEQ ID NOS: 17

<210> SEQ ID NO 1
<211> LENGTH: 6
<212> TYPE: PRT
<213> ORGANISM: Artificial Sequence
<220> FEATURE:
<223> OTHER INFORMATION: synthetic peptide

<400> SEQUENCE: 1

Ala Ala Ala Ala Ala Lys
1               5

<210> SEQ ID NO 2
<211> LENGTH: 7
<212> TYPE: PRT
<213> ORGANISM: Artificial Sequence
<220> FEATURE:
```

<223> OTHER INFORMATION: synthetic peptide

<400> SEQUENCE: 2

Ala Ala Ala Ala Ala Ala Lys
1               5

<210> SEQ ID NO 3
<211> LENGTH: 8
<212> TYPE: PRT
<213> ORGANISM: Artificial Sequence
<220> FEATURE:
<223> OTHER INFORMATION: synthetic peptide

<400> SEQUENCE: 3

Ala Ala Ala Ala Ala Ala Ala Lys
1               5

<210> SEQ ID NO 4
<211> LENGTH: 7
<212> TYPE: PRT
<213> ORGANISM: Artificial Sequence
<220> FEATURE:
<223> OTHER INFORMATION: synthetic peptide

<400> SEQUENCE: 4

Ala Ala Ala Ala Ala Lys Lys
1               5

<210> SEQ ID NO 5
<211> LENGTH: 8
<212> TYPE: PRT
<213> ORGANISM: Artificial Sequence
<220> FEATURE:
<223> OTHER INFORMATION: synthetic peptide

<400> SEQUENCE: 5

Ala Ala Ala Ala Ala Ala Lys Lys
1               5

<210> SEQ ID NO 6
<211> LENGTH: 9
<212> TYPE: PRT
<213> ORGANISM: Artificial Sequence
<220> FEATURE:
<223> OTHER INFORMATION: synthetic peptide

<400> SEQUENCE: 6

Ala Ala Ala Ala Ala Ala Ala Lys Lys
1               5

<210> SEQ ID NO 7
<211> LENGTH: 6
<212> TYPE: PRT
<213> ORGANISM: Artificial Sequence
<220> FEATURE:
<223> OTHER INFORMATION: synthetic peptide

<400> SEQUENCE: 7

Ala Ala Ala Ala Ala Arg
1               5

<210> SEQ ID NO 8
<211> LENGTH: 7
<212> TYPE: PRT
<213> ORGANISM: Artificial Sequence
<220> FEATURE:
<223> OTHER INFORMATION: synthetic peptide

```
<400> SEQUENCE: 8

Ala Ala Ala Ala Ala Ala Arg
1               5

<210> SEQ ID NO 9
<211> LENGTH: 8
<212> TYPE: PRT
<213> ORGANISM: Artificial Sequence
<220> FEATURE:
<223> OTHER INFORMATION: synthetic peptide

<400> SEQUENCE: 9

Ala Ala Ala Ala Ala Ala Ala Arg
1               5

<210> SEQ ID NO 10
<211> LENGTH: 7
<212> TYPE: PRT
<213> ORGANISM: Artificial Sequence
<220> FEATURE:
<223> OTHER INFORMATION: synthetic peptide

<400> SEQUENCE: 10

Ala Ala Ala Ala Ala Arg Arg
1               5

<210> SEQ ID NO 11
<211> LENGTH: 8
<212> TYPE: PRT
<213> ORGANISM: Artificial Sequence
<220> FEATURE:
<223> OTHER INFORMATION: synthetic peptide

<400> SEQUENCE: 11

Ala Ala Ala Ala Ala Ala Arg Arg
1               5

<210> SEQ ID NO 12
<211> LENGTH: 9
<212> TYPE: PRT
<213> ORGANISM: Artificial Sequence
<220> FEATURE:
<223> OTHER INFORMATION: synthetic peptide

<400> SEQUENCE: 12

Ala Ala Ala Ala Ala Ala Ala Arg Arg
1               5

<210> SEQ ID NO 13
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (7)..(7)
<223> OTHER INFORMATION: Xaa is homoarginine

<400> SEQUENCE: 13

Ala Ala Ala Ala Ala Ala Xaa
1               5

<210> SEQ ID NO 14
<211> LENGTH: 7
<212> TYPE: PRT
```

```
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (7)..(7)
<223> OTHER INFORMATION: Xaa is Orn

<400> SEQUENCE: 14

Ala Ala Ala Ala Ala Ala Xaa
1               5

<210> SEQ ID NO 15
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (7)..(7)
<223> OTHER INFORMATION: Xaa is 2,7-diaminoheptanoic acid

<400> SEQUENCE: 15

Ala Ala Ala Ala Ala Ala Xaa
1               5

<210> SEQ ID NO 16
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (7)..(7)
<223> OTHER INFORMATION: Xaa is Dbu

<400> SEQUENCE: 16

Ala Ala Ala Ala Ala Ala Xaa
1               5

<210> SEQ ID NO 17
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (7)..(7)
<223> OTHER INFORMATION: Xaa is 2-amino-4-guanidinobutyric acid

<400> SEQUENCE: 17

Ala Ala Ala Ala Ala Ala Xaa
1               5
```

BSH COMPLEX FOR BORON NEUTRON CAPTURE THERAPY

TECHNICAL FIELD

The present invention relates to a drug for a cancer therapy and a method for producing the same. Specifically, the present invention relates to a complex of mercaptoundecahydrododecaborate (BSH) and a peptide for boron neutron capture therapy (BNCT), a method for producing the same, and a cancer therapy using the same.

BACKGROUND ART

Boron neutron capture therapy (BNCT) is an excellent method for treating a cancer, in which boron isotope $^{10}B$ is introduced into a cancer cell and a neutron beam is irradiated to kill only the cancer cell, and QOL after treatment is also excellent. It is the biggest challenge for BNCT to safely and easily deliver a sufficient amount of a boron drug into a cancer cell. BPA which is an amino acid derivative containing one boron atom has been used as a main agent and BSH which does not enter a cell itself including a cancer cell has been used as a secondary agent (see Non Patent Literatures 1 and 2).

BPA is taken into a cell by an amino acid transporter present in the cell membrane. However, because even normal cells, in case they are aggressively proliferating cells such as mucosal epithelial and hair growth cells, take PBA actively, the neutron irradiation also damages these normal cells. Additionally, BPA, which is taken into a cell through an amino acid transporter (LAT1 is presumed to be primarily responsible), is not easily retained in a cell, a cancer cell, in a large amount because such an amino acid transporter is an "exchanger (see Non Patent Literature 3)", and further BPA has only one boron atom per molecule, which causes a poor collision efficiency against a neutron beam, whereby a large amount needs to be administered (several tens g per adult) to deliver and retain necessary boron in a cancer cell.

BSH is a crystal having 12 boron atoms per molecule and thus has a high efficiency. However, BSH does not permeate the cell membrane and thus does not enter a cell as it is. BSH leaks from fragile blood vessels of cancer tissues, goes into the interstitial fluid, and is simply stored around cells. For this reason, it is difficult that secondary particles (α particle, Li nucleus) generated by the neutron irradiation reach the cell nucleus where an influential gene DNA is present, whereby a sufficient killing effect cannot be obtained. Further, BSH lacks in cancer cell specificity, which is also problematic.

Various nanocarriers are currently proposed in addition to the boron drugs, BPA and BSH, which have been clinically used so far. These are classified into liposome (lipid bilayer vesicle), polymeric micelle (amphiphilic polymer vesicles), and carbon nanotube, however pose the following problems. Liposome releases a drug continuously and is physically unstable while low in toxicity. Polymeric micelle is preferable in biocompatibility and biodegradability but has short in vivo half-life. Carbon nanotube has a wide surface area but does not have cargo selectivity and is toxic.

CITATION LIST

Non Patent Literature

Non Patent Literature 1: Kato I. et al., Appl. Radiat. Isot. 2004; 61: 1069-73

Non Patent Literature 2: Hatanaka H. et al., J. Neurol. 1975; 209: 81-94

Non Patent Literature 3: Biochemistry, vol. 86, No. 3, pp 338-344 (2014))

SUMMARY OF INVENTION

Problem to be Solved by the Invention

The problem to be solved by the present invention is to provide a drug capable of directly delivering and retaining BSH in a cancer cell thereby to enable BNCT to be carried out efficiently.

Means to Solve the Problem

The inventors conducted extensive studies to solve the above problems, and have found that a complex comprising a peptide containing a hydrophobic amino acid residue and a basic amino acid residue and BSH, obtained by mixing the peptide with BSH in an aqueous solution is in a spherical shape having a diameter of about 20 nm to about 200 nm, which is the ideal shape for cell introduction, and directly delivered to and retained in a cancer cell, whereby the present invention has been accomplished.

Specifically, the present invention provides the following:
(1) a method for producing a complex comprising a peptide containing a hydrophobic amino acid residue and a basic amino acid residue and mercaptoundecahydrododecaborate (BSH), said method comprising mixing the peptide with BSH in an aqueous solution;
(2) the method according to (1), wherein BSH is mixed in a ratio of 1 mol to 1000 mol, to 1 mol of the peptide;
(3) the method according to (1) or (2), further comprising adjusting a diameter of the complex;
(4) the method according to any one of (1) to (3), wherein the complex is in a spherical form having a diameter of about 20 nm to about 200 nm;
(5) the method according to any one of (1) to (4), wherein the peptide is represented by the following formula (1):

[Formula 1]

wherein m number of amino acid residues X are each independently alanine, valine, leucine, or glycine; n number of amino acid residues Z are each independently —NHCH(COOH)R$^1$; R$^1$ is —(CH$_2$)$_p$NHR$^2$; R$^2$ is —H or —C(NH)NH$_2$; m is 4 to 10; n is 1 to 2; and p is 1 to 6;
(6) the method according to (5), wherein X is alanine; m is 6; Z is lysine, arginine, homoarginine, ornithine, 2,7-diaminoheptanoic acid, 2,4-diaminobutyric acid, or 2-amino-4-guanidinobutyric acid; and n is 1;
(7) the method according to (6), wherein X is alanine; m is 6; Z is lysine or arginine; and n is 1;
(8) a complex comprising a peptide containing a hydrophobic amino acid residue and a basic amino acid residue and BSH;
(9) the complex according to (8), wherein the complex is in a spherical shape having a diameter of about 20 nm to about 200 nm;
(10) the complex according to (8) or (9), wherein the peptide is represented by the following formula (1):

[Formula 2]

wherein an m number of the amino acid residues X are each independently alanine, valine, leucine, or glycine; n number of amino acid residues Z are each independently —NHCH(COOH)$R^1$; $R^1$ is —$(CH_2)_p NHR^2$; $R^2$ is —H or —$C(NH)NH_2$; m is 4 to 10; n is 1 to 2; and p is 1 to 6;

(11) the complex according to (10), wherein X is alanine; m is 6; Z is lysine, arginine, homoarginine, ornithine, 2,7-diaminoheptanoic acid, 2,4-diaminobutyric acid, or 2-amino-4-guanidinobutyric acid; and n is 1;

(12) the complex according to (11), wherein X is alanine; m is 6; Z is lysine or arginine; and n is 1;

(13) a drug for boron neutron capture therapy of a cancer, comprising the complex according to any one of (8) to (12);

(14) a method for treating a cancer, comprising administering the complex according to any one of (8) to (12) to a cancer patient and irradiating the cancer patient with a neutron beam;

(15) the complex according to any one of (8) to (12), for use in boron neutron capture therapy of a cancer; and

(16) use of the complex according to any one of (8) to (12), for producing a drug for boron neutron capture therapy of a cancer.

Effects of Invention

According to the present invention, a complex capable of delivering and retaining a large amount of BSH in a cancer cell can be obtained by a simple operation such as mixing a peptide containing a hydrophobic amino acid residue and a basic amino acid residue with BSH in an aqueous solution. The ratio of such a peptide to BSH desirably ranges from equal amounts up to an excess amount of 1000 times molar ratio of BSH. When a complex of the present invention is used, the effect of BNCT is notably enhanced. For example, the delivery and retention of BSH in a cancer cell is surely enabled by a single injection.

BRIEF DESCRIPTION OF DRAWINGS

The patent or application file contains at least one drawing executed in color. Copies of this patent or patent application publication with color drawing(s) will be provided by the Office upon request and payment of the necessary fee.

DESCRIPTION OF EMBODIMENTS

Figure 1:
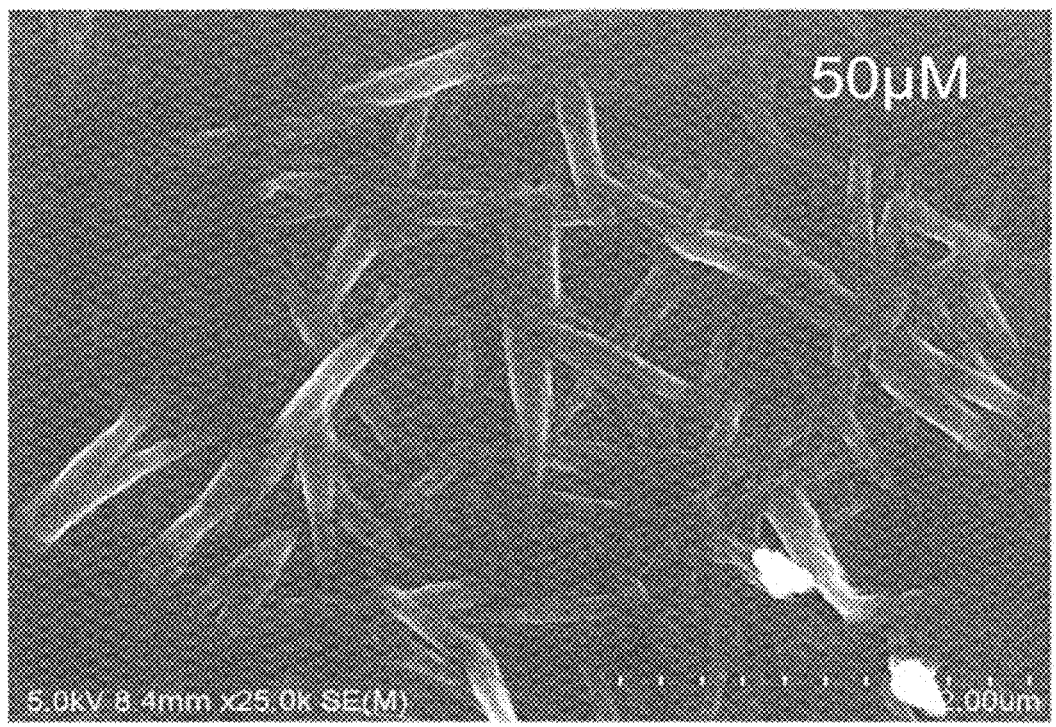
FIG. 1 shows a scanning electron micrograph of A6K (trifluoroacetate, hereafter referred to as TFA salt) in an aqueous solution (concentration 50 μM). A bar at bottom right is 2 microns.

The present invention provides, in an embodiment, a method for producing a complex comprising a peptide containing a hydrophobic amino acid residue and a basic amino acid residue and BSH, said method comprising mixing the peptide with BSH in an aqueous solution. Hydrophobic amino acids and basic amino acids are well known. Various kinds of the peptides are also known containing a hydrophobic amino acid residue and a basic amino acid residue, which can be used in the present invention. In the present invention, the peptide containing a hydrophobic amino acid residue and a basic amino acid residue preferably used is represented by the following formula (1):

[Formula 3]

$(X)_m—(Z)_n$ (1)

wherein m number of amino acid residues X are each independently alanine, valine, leucine, or glycine; n number of amino acid residues Z are each independently —NHCH(COOH)$R^1$; $R^1$ is —(CH$_2$)$_p$NHR$^2$; $R^2$ is —H or —C(NH)NH$_2$; m is 4 to 10; n is 1 to 2; and p is 1 to 6. In the present invention, examples of the more preferably used peptide containing a hydrophobic amino acid residue and a basic amino acid residue include XXXXXZZ, XXXXXXZ, XXXXXXXZ, XXXXXXXZZ, XXXXXXXZ, and XXXXXXXZZ, but not limited thereto. Specific examples of these peptides include AAAAAK (SEQ ID NO: 1), AAAAAAK (SEQ ID NO: 2), AAAAAAAK (SEQ ID NO: 3), AAAAAKK (SEQ ID NO: 4), AAAAAAKK (SEQ ID NO: 5), AAAAAAAKK (SEQ ID NO: 6), AAAAAR (SEQ ID NO: 7), AAAAAAR (SEQ ID NO: 8), AAAAAAAR (SEQ ID NO: 9), AAAAARR (SEQ ID NO: 10), AAAAAARR (SEQ ID NO: 11), and AAAAAAARR (SEQ ID NO: 12). In the present invention, further specific examples of the more preferably used peptide containing a hydrophobic amino acid residue and a basic amino acid residue include AAAAAA-homoarginine (SEQ ID NO: 13), AAAAAA-ornithine (SEQ ID NO: 14), AAAAAA-2,7-diaminoheptanoic acid (SEQ ID NO: 15), AAAAAA-2,4-diaminobutyric acid (SEQ ID NO: h), and AAAAAA-2-amino-4-guanidinobutyric acid (SEQ ID NO: 17). In the present invention, typical examples of the more preferably used peptide described above include AAAAAAK (abbreviated as A6K; SEQ ID NO: 2) and AAAAAAR (abbreviated as A6R; SEQ ID NO: 8). When there is a modifiable moiety in the amino acid residues X and Z, the amino acid residues X and Z may be modified. Additionally, 1 or 2 amino acid residues in the peptide represented by the formula (1) may be substituted with amino acid residues other than the hydrophobic amino acid residue or basic amino acid residue. In a method for producing a complex of the present invention, the peptide may be in the free form, in the salt form, in the solvate form, or modified or derivatized. Various salts of a peptide are well known and the production methods thereof are also well known. Examples of the salt of a peptide include a hydrochloride salt, a sulfate, a nitrate, a phosphate, an acetate, a trifluoroacetate (TFA salt), a citrate, a succinate, a maleate, a fumarate, a malate, a tartrate, a p-toluenesulfonate, a benzenesulfonate, a methanesulfonate, an alkali metal salt, and an alkaline earth metal salt, but not limited thereto. Solvates of a peptide are also well known and the production method thereof are also well known. Example of the solvate of a peptide include solvates of water, methanol, ethanol, isopropanol, THF, DMSO, ethylene glycol, propylene glycol, and acetamide, but not limited thereto. Various modified peptides and peptide derivatives are well known. Methods of modification and derivatization of a peptide are also well known. Examples of the modification and derivatization of a peptide include alkylation such as acetylation, amidation, biotinylation, maleimidation, and methylation, maleimidation, myristoylation, esterification, phosphorylation, and labellation such as fluorescent labelling, and radiolabelling, but not limited thereto. An N-terminal of a peptide is preferably acetylated. Further, the amino acids constituting a peptide may be natural amino acids or non-natural amino acids, and may be the L-form or D-form. In the present invention, the peptide, when referred, encompasses a modified peptide, a derivatized peptide, a salt form peptide, an amino acid-substituted peptide, and a peptide-containing D-amino acid as described above. The peptides listed above as examples are shown by the conventional one-letter amino acid codes.

BSH is also well known and a crystal having 12 boron isotope $^{10}$B in a molecule. As described above, BSH has many boron atoms per molecule and, when used for BNCT, has a high collision efficiency against a neutron beam. However, a cancer cell killing effect by BNCT is low because BSH cannot permeate the cell membrane and thus does not enter a cell as it is. In the present invention, a complex comprising a peptide containing a hydrophobic amino acid residue and a basic amino acid residue and BSH is constructed, thereby successfully to deliver and retain BSH in a cancer cell. In this way, a cancer cell killing effect by BNCT can be notably enhanced and safety is ensured simultaneously. In a method for producing a complex of the present invention, BSH may be modified or derivatized. Modified BSH and derivatized BSH are well known and examples include peptide-bound BSH, saccharide-bound BSH, and BSH having a thiol group, a hydroxyl group, a carboxyl group, an amino group, an amide group, an azide group, a halogen group, and a phosphoric acid group are shown, but not limited thereto. Methods for producing a modified BSH and a derivatized BSH are also well known.

A complex of the present invention comprising a peptide containing a hydrophobic amino acid residue and a basic amino acid residue and BSH can be obtained by mixing the peptide with BSH in an aqueous solution. This operation is very simple. When mixing, stirring or ultrasonication may be carried out if necessary. The concentration of the peptide in an aqueous solution is not particularly limited and generally several μM to several thousands μM. The concentration of BSH in an aqueous solution is not also particularly limited and generally several tens μM to several thousands μM. The molar ratio of the above peptide to BSH to be mixed is not also particularly limited but mixing ratio is preferably a ratio of about 1 mol to about 1000 mol of BSH to 1 mol of the peptide, and for example, a ratio of about 1 to about 100 mol of BSH to 1 mol of the peptide, and may be a ratio of about 100 to about 1000 mol of BSH to 1 mol of the peptide.

The aqueous solution used for the mixing to produce the complex comprising the peptide containing a hydrophobic amino acid residue and a basic amino acid residue and BSH is a solution having water as a medium. The aqueous solution may be only water, or other substances such as a buffer or salts may be added thereto. The conditions such as temperature, pH, and mixing time at the time of mixing may be determined if necessary by a person skilled in the art. For example, when BSH and A6K or A6R are mixed, it is preferable to mix under conditions that lysine residues of A6K or arginine residues of A6R are positively charged and BSH is negatively charged. pH of the aqueous solution may be adjusted to a desired value using a buffer such as PBS.

The shape of the complex comprising the peptide containing a hydrophobic amino acid residue and a basic amino acid residue and BSH, obtained by the method of the present invention is a spherical shape with horn-like prongs on the surface or a spherical shape without such a prong. The spherical shape encompasses not only the perfect sphere but also approximate spheres. Specifically, a shape can be defined as a spherical shape when a ratio of a minor axis to a major axis is about 0.5 or more, preferably about 0.6 or more, and further preferably about 0.7 or more. The diameter of a complex obtained by the present invention is about 20 nm to about 200 nm. The diameter of a complex is an average of a major axis and a minor axis, and when a spherical shape has horn-like prongs, the diameter includes the prong parts. The diameter of a complex of the present invention can be measured, for example, by using an electron microscope. In the present description, for example, when "the diameter of a complex is about 20 nm to about 200 nm" is referred, it means that a diameter of the most part of a complex, for example, about 50% or more, preferably about 60% or more, and further preferably about 70% or more, is about 20 nm to about 200 nm.

In various DDS carriers, a major factor associated with drug delivery is the size of a complex of a drug and a carrier. When a diameter of the complex is too large, the leakage from tumor vessels is difficult, causing low tumor reachability. When a diameter is too small, a drug retentivity at a tumor part becomes low, causing a low concentration of the drug. The ideal value of a complex of a drug and a carrier reported so far is about 20 to 100 nm. In other words, when an EPR effect by increased vessel permeability around a cancer tissue site is expected, the diameter is about 100 nm, but in the case of refractory cancer accompanied by chronic inflammation, the diameter is said to be about 20 nm to 30 nm. A diameter of a complex of the present invention is, as described later, about 20 nm to about 200 nm, for example, about 20 nm to 100 nm, which is close to the ideal value, whereby both tumor reachability and drug retentivity are high.

According to a production method of the present invention, many complexes having a diameter of about 20 nm to about 200 nm can be obtained simply by mixing a peptide and BSH. Thus, the complex obtained by a production method of the present invention may be used as it is for BNCT. When a ratio of BSH to a peptide to be mixed is low, many complexes have small diameters, whereas when a ratio of BSH to a peptide is high, many complexes have large diameters. Using this property, a diameter of the complex can be adjusted. Alternatively, a diameter of the complex may be adjusted using a filter having a desired pore size or an extruder having a desired pore size.

In another embodiment, the present invention provides a complex comprising a peptide containing a hydrophobic amino acid residue and a basic amino acid residue and BSH. The complex of the present invention is in a spherical shape having a diameter of about 20 nm to about 200 nm.

The present invention provides, in further another embodiment, a drug for BNCT of a cancer containing the above complex. The complex of the present invention can deliver and retain BSH in a cancer cell efficiently. For this reason, a drug containing the complex of the present invention can significantly enhance the effect of BNCT.

A cancer subjectable to the therapy using a drug of the present invention may be any kind of cancers and is not particularly limited. Examples of the cancer subjectable to the therapy using a drug of the present invention include esophagus cancer, stomach cancer, colorectal cancer, liver cancer, gallbladder cancer, bile duct cancer, pancreas cancer, renal cell cancer, gastrointestinal stromal tumor, mesothelioma, brain tumor (meningioma, glioma, pituitary tumor, acoustic neuroma, glioblastoma multiforme, etc.), head and neck cancer, laryngeal cancer, oral cancer, cancer of the floor of the mouth, gingiva cancer, tongue cancer, buccal mucosa cancer, salivary gland cancer, paranasal sinus cancer, maxillary sinus cancer, frontal sinus cancer, ethmoid sinus cancer, sphenoidal sinus cancer, thyroid cancer, lung cancer, osteosarcoma, bladder cancer, prostate cancer, testicular tumor, testicular cancer, penile cancer, breast cancer, endometrial cancer, cervical cancer, ovarian cancer, skin cancer, rhabdomyosarcoma, leukemia, lymphoma, Hodgkin disease, non-Hodgkin lymphoma, and multiple myeloma, but not limited thereto.

A complex of the present invention may be used as a drug for BNCT as it is, or may be formulated to various dosage forms using a pharmaceutically acceptable carrier or excipient by a method well known by a person skilled in the art. The carrier or excipient used are well known by a person skilled in the art and can be selected if necessary. A drug of the present invention can be produced using a means and a method well known by a person skilled in the art. For example, when an injection and a transfusion are produced, a pharmaceutically acceptable carrier such as saline or phosphate buffered saline can be used. For preparing a drug of the present invention, pharmaceutically acceptable additives such as a thickener, an absorption promoter, a pH adjusting agent, a preservative, a dispersant, a wetting agent, a stabilizer, an antiseptic, a suspension, and a surfactant may be used.

The dosage form of a drug of the present invention is not particularly limited and can be selected if necessary depending on a site, a size, a kind of a cancer to be treated, and conditions of a patient. A drug of the present invention may be in a liquid form, a semi-solid form, or a solid form. Examples of the dosage form of a drug of the present invention include an injection, an infusion, a nasal drop, an ophthalmic solution, a lotion, a spray, a cream, a gel, an ointment, a suppository, a table, a capsule, a powder, a granule, a syrup, an aerosol, a transdermal agent, a transmucosal agent, and an inhaler, but not limited thereto. Alternatively, a drug of the present invention may be in the form of a lyophilized product wherein the drug is suspended, when administered, in a pharmaceutically acceptable carrier such as saline or phosphate buffered saline.

The administration route of a drug of the present invention is not particularly limited and can be selected if necessary depending on a site, a size, a kind of a cancer to be treated, and conditions of a patient. Examples of the administration route of a drug of the present invention include local administrations such as a subcutaneous injection, an intradermal injection, an intravenous injection, an infusion, oral administration, transmucosal administration, enteral administration, ophthalmic administration, nasal administration, ear dripping, inhalation, transdermal administration, and intratumoral administration, and intraventricular administration, but not limited thereto.

The dose of a drug of the present invention can be determined if necessary by a physician depending on a site, a size, a kind of a cancer to be treated, and conditions of a patient.

After a drug of the present invention is administered to a patient and enough time has passed for the complex of the present invention to reach a site to be treated, a neutron beam is subsequently irradiated. At the time of neutron irradiation, a reactor or an accelerator-type neutron generator is used and necessary conditions for the therapy such as a neutron beam dose and a neutron spectrum and irradiation time are determined.

The administration of a drug of the present invention and neutron irradiation can be carried out once to several times. The number of times can be determined by a physician in consideration of a site and a kind of a cancer, a degree of decreased cancer size, and conditions of a patient.

The present invention provides, in another embodiment, a use of the above complex for producing a drug for BNCT of cancer.

The present invention provides, in another embodiment, a use of the above complex for BNCT of cancer.

The present invention provides, in another embodiment, a cancer therapy method comprising administering the above complex to a cancer patient and irradiating the patient with neutron.

Hereinafter, the present invention is further specifically described in detail in reference to examples but the examples should not be understood to limit the scope of the present invention.

Example 1

(1) Shape of A6K (TFA Salt) in an Aqueous Solution

Figure 2:
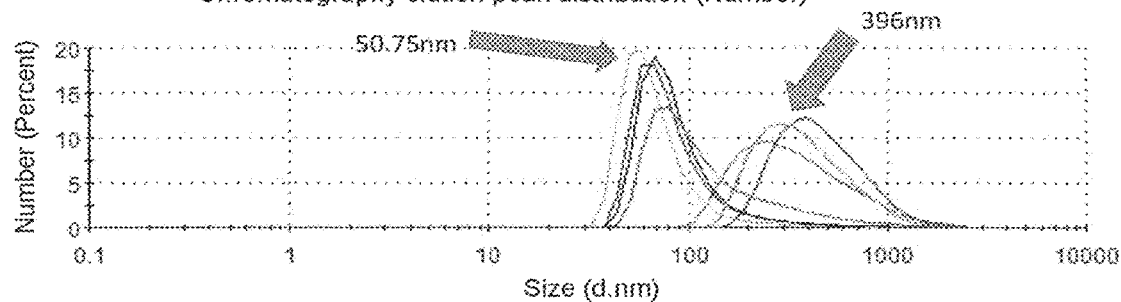
FIG. 2 is a chart showing results of Dynamic Light Scanning (DLS) test of A6K (TFA salt) in an aqueous solution (concentration 200 μM).

A lyophilized product of A6K (TFA salt) synthesized by a routine method was dissolved in Milli-Q water (concentration 1000 µM) and pH was adjusted to 4 with HCl. Ultrasonication was carried out for 10 minutes to adjust pH to 7 with NaOH. The obtained solution was allowed to pass through an extruder having a pore size of 100 nm and diluted to a concentration of 50 µM with Milli-Q water. Of the solution, 1.2 µL was separated as a sample and observed using a scanning electron microscope. The scanning electron micrograph is shown in FIG. 1. A6K (TFA salt) was found to have a tubular form. A solution of A6K (TFA salt) having a concentration of 200 µM prepared in a similar manner to the above was subjected to DLS test. The chart is shown in FIG. 2. In the chart, bimodal peaks were observed, verifying that A6K (TFA salt) was tubular.

(2) Production of a Complex Containing A6K (TFA Salt) and BSH

Figure 3:
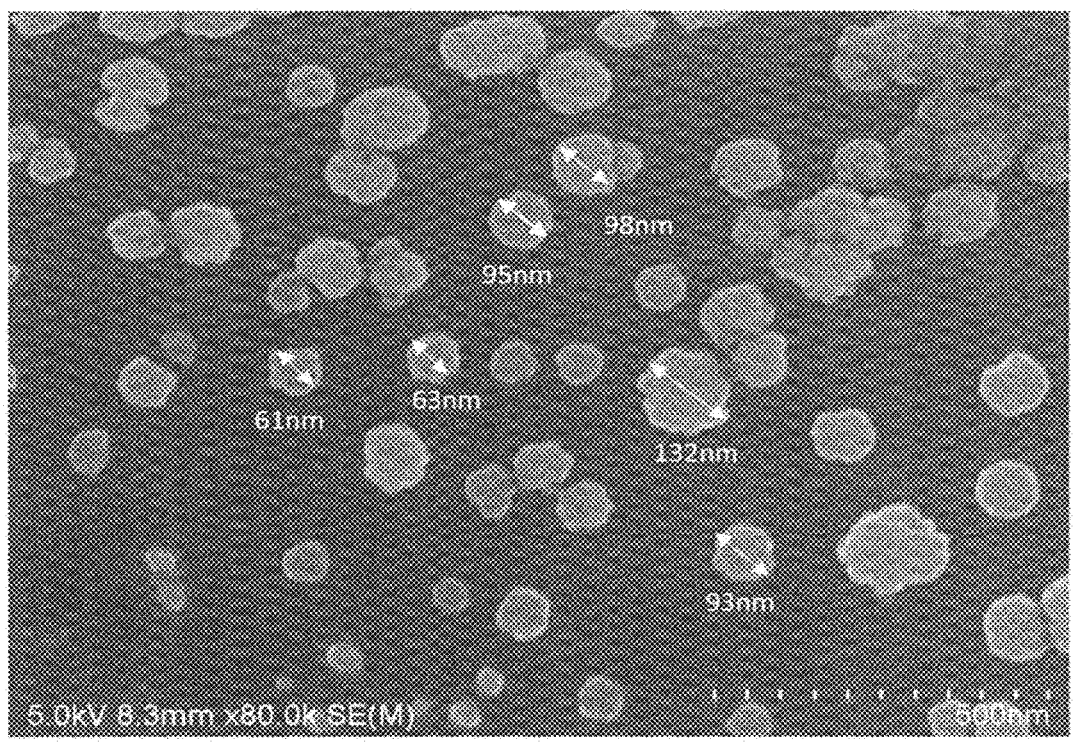
FIG. 3 is a scanning electron micrograph of a complex obtained by mixing A6K (TFA salt) (10 μM) and BSH (1000 μM) in an aqueous solution. A bar at bottom right is 500 nm.
Figure 4:
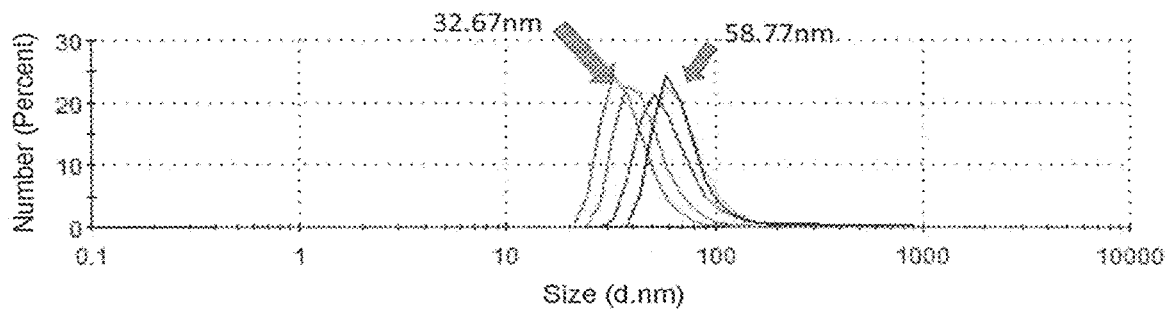
FIG. 4 is a chart showing results of DLS test of a complex obtained by mixing A6K (TFA salt) (200 μM) and BSH (2000 μM) in an aqueous solution.

An aqueous solution of A6K (TFA salt) in Milli-Q water (10 µm) was obtained in a similar manner to that in the above (1). BSH was added (concentration 1000 µM) and mixed with stirring at room temperature for 3 minutes to observe the obtained complex using a scanning electron microscope. The result is shown in FIG. 3. The complex was found to be in a spherical shape having horn-like prongs (kompei-to shape) and most of them had a diameter ranging from about 20 nm to about 150 nm. A complex obtained by mixing A6K (TFA salt) (200 µM) and BSH (2000 µM) in a similar manner to that above was subjected to DLS test. The results are shown in FIG. 4. Bimodal peaks adjacent to each other were observed, verifying that the complex was in an approximately spherical shape. These results show that the shape and size of the obtained complex are optimum for delivering BSH into a cancer cell.

(3) Delivery of a Complex into a Cancer Cell

Figure 5:
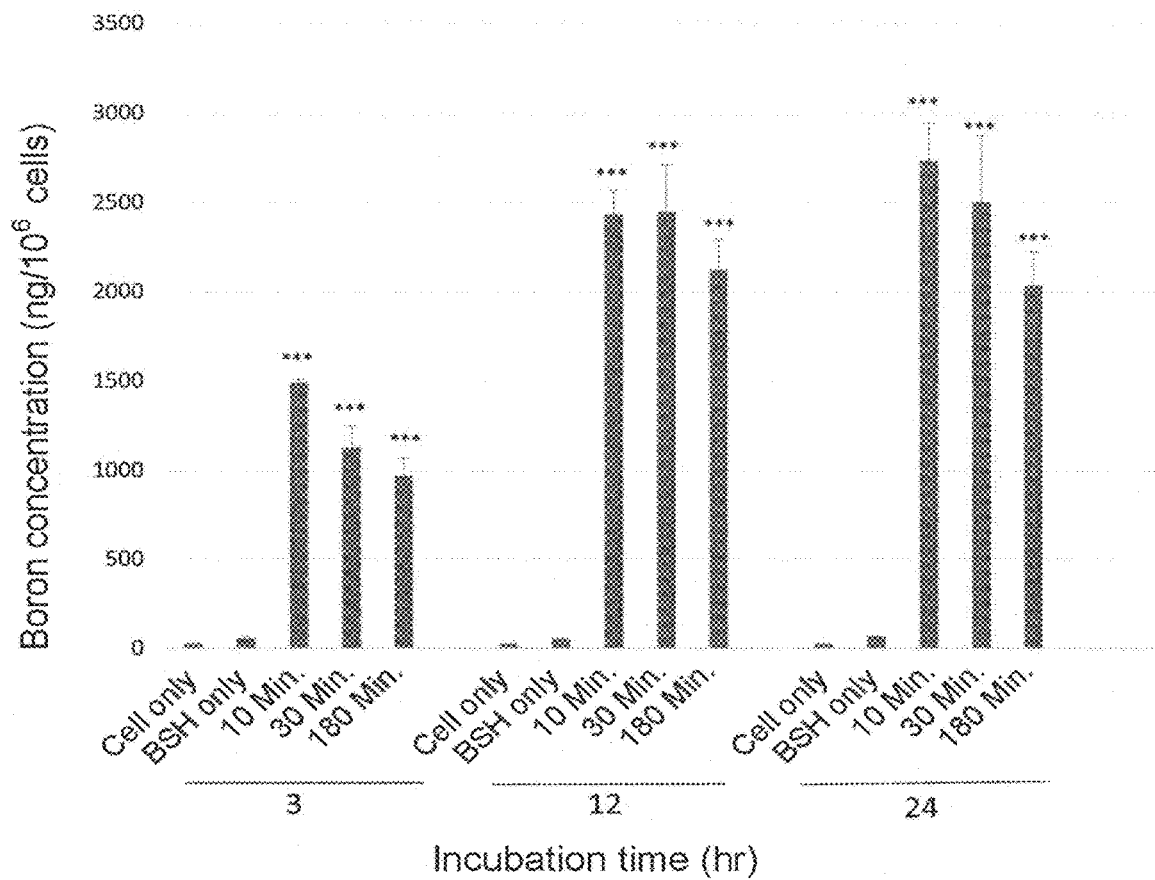
FIG. 5 is a graph showing the effect of the mixing time of A6K (TFA salt) and BSH and the incubation time of a complex and U87ΔEGFR cells, on an amount of the complex delivered into the cell. The effect was investigated, using Inductively Coupled Plasma-Atomic Emission Spectroscopy (ICP-AES). *** is p<0.005.

A6K (TFA salt) and BSH were mixed with stirring by the same method as the method described in the above (2) to prepare a complex. Mixing times were 10 minutes, 30 minutes, and 180 minutes. The obtained complex was diluted (pH 7.1 to 7.3) with PBS and added to a glioma cell line U87ΔEGFR in a petri dish. The complex was added in an amount in such a way that a final concentration of A6K (TFA salt) was 50 µM and a final concentration of BSH was 5000 µM. Each cell sample obtained by incubating, with the complex, at 37° C. for 3 hours, 12 hours, and 24 hours was subjected to ICP-AES thereby to measure a boron concentration in the cell. The results are shown in FIG. 5. The complex was taken into the cell under all conditions. It was found that a large amount of the complex was taken into in 12-hour and 24-hour incubations. The incubation time of 12 hours was sufficient. The time for mixing with stirring did not much affected delivery amounts of the complex into a cancer cell. The time for mixing with stirring of 10 minutes was sufficient. Increases in the BSH amounts in the cell were detected as an incubation time was extended. Thus, it was confirmed that the present complex had the retentivity in a cancer cell.

Example 2

(1) Production of a Complex Containing A6R (TFA Salt) and BSH

Figure 6:
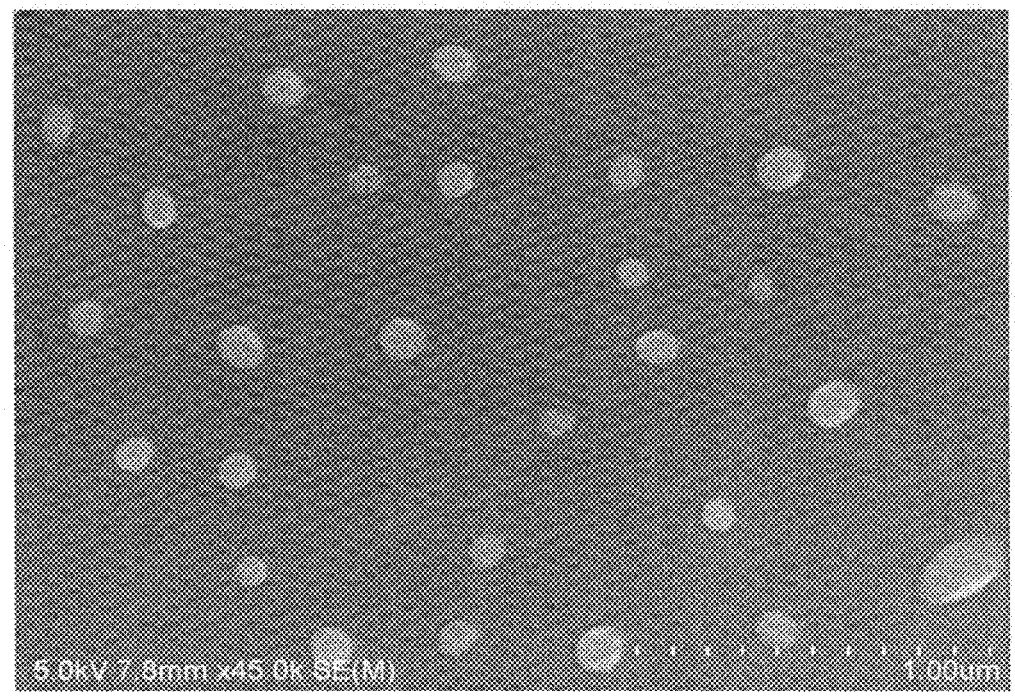
FIG. 6 is a scanning electron micrograph of a complex obtained by mixing A6R (TFA salt) (10 μM) and BSH (1000 μM) in an aqueous solution. A bar at a bottom right is 1 micron.

A lyophilized product of A6R (TFA salt) synthesized by a routine method was dissolved in Milli-Q water (concentration 1000 µM) and pH was adjusted to 4 with HCl. Ultrasonication was carried out for 10 minutes to adjust pH to 7 with NaOH. The obtained solution was diluted to a concentration of 10 µm with Milli-Q water. BSH was added (concentration 1000 µm) to the aqueous solution (10 µM) of the thus obtained A6R (TFA salt) in Milli-Q, mixed with stirring at room temperature for 3 minutes and subjected to ultrasonication for 10 minutes, and subsequently allowed to pass through an extruder having a pore size of 50 nm to obtain a complex. The obtained complex was observed using a scanning electron microscope. The result is shown in FIG. 6. The complex was found to be in a spherical shape and most of them had a diameter ranging from about 100 nm to about 200 nm. Further, when a complex was prepared in a similar manner to the above except that a molar ratio of A6R (TFA salt) to BSH was 1:1 (20 µM:20 µM), the size of the complex was smaller, most of them had a diameter of about 50 nm to about 150 nm, including those with a diameter of about 20 nm.

(2) Delivery of a Complex into a Cancer Cell

Figure 7:
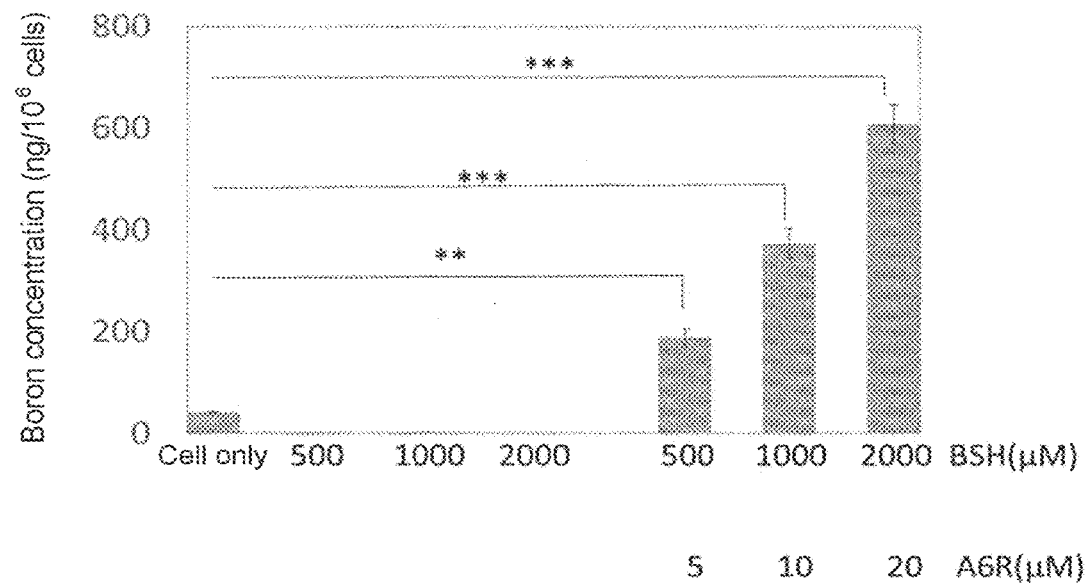
FIG. 7 is a graph showing concentration-dependent cell introduction of a complex obtained by mixing A6R (TFA salt) and BSH in an aqueous solution. An amount of the complex delivered into the cell was investigated using Inductively Coupled Plasma-Atomic Emission Spectroscopy (ICP-AES).  is p<0.01, and * is p<0.001.
Figure 8:
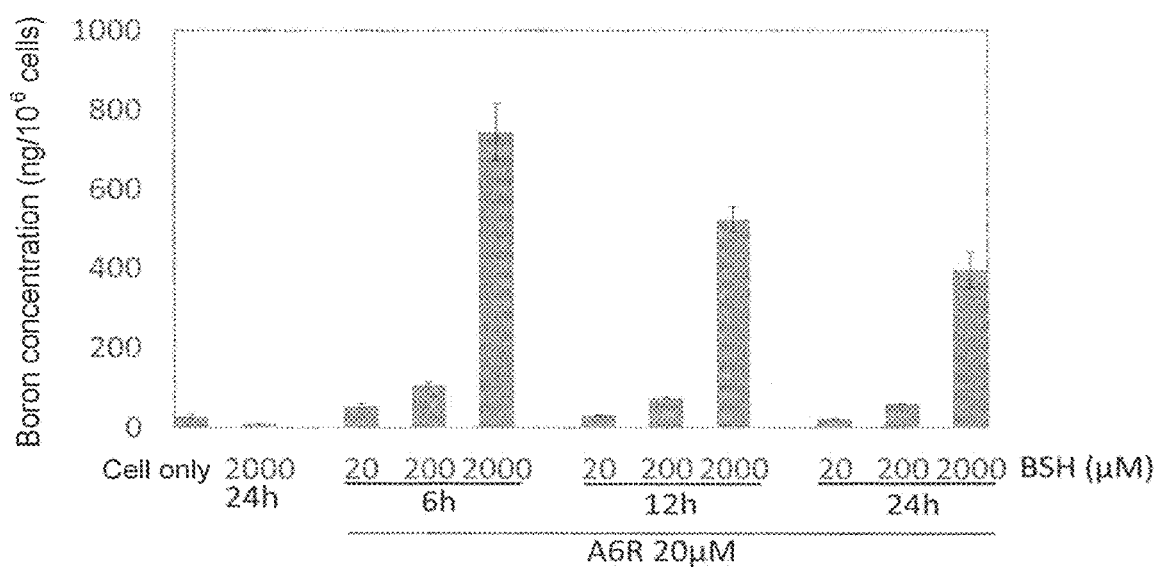
FIG. 8 is a graph showing the effect of the incubation time of U87ΔEGFR cells and a complex obtained by mixing A6R (TFA salt) and BSH in an aqueous solution, on an amount of the complex delivered into the cell. The effect was investigated, using Inductively Coupled Plasma-Atomic Emission Spectroscopy (ICP-AES).

A6R (TFA salt) and BSH were mixed with stirring by the same method as the method described in the above (1) to prepare a complex. The obtained complex was diluted (pH 7.1 to 7.3) with PBS and added to a glioma cell line U87ΔEGFR in a petri dish. The complex was added in an amount in such a way that final concentrations of A6R (TFA salt) and BSH as shown in FIG. 7 and FIG. 8. Each cell sample obtained by incubating, with the complex, at 37° C. for 6 hours, 12 hours, and 24 hours was subjected to ICP-AES thereby to measure a boron concentration in the cell. The results are shown in FIG. 7 and FIG. 8. As shown in FIG. 7, it was confirmed that the complex of A6R (TFA salt) and BSH was introduced into the cell in a concentration-dependent manner. Further, as shown in FIG. 8, the incubation time of 6 hours was sufficient. A considerable amount of the complex also remained in the cell after 12-hour incubation and 24-hour incubation, confirming that the present complex had the retentivity in a cancer cell.

Example 3

The subcellular distribution of a complex of the present invention was investigated.

(1) Experimental Method

U87ΔEFGR cells were inoculated on a glass plate (PLL coat, 12 mm: manufactured by IWAKI & Co., Ltd.) in a 24-well plate (manufactured by Falcon) (3000 cells/well, 1 ml in each well) and incubated in a $CO_2$ incubator at 37° C. for 24 hours, to which a complex containing A6K (TFA salt) and BSH prepared by the same method as Example 1 (2) was added. The complex was added in an amount in such a way that a final concentration of A6K (TFA salt) was 20 µM and a final concentration of BSH was 2000 µM. After the complex was added and the cells were incubated for 90 minutes, the cell incubation liquid was removed, 1 ml of PBS (Phosphate Buffered Saline) was added at room temperature, the cells were allowed to stand for 5 minutes, subsequently removed and washed 3 times (1 ml each for 5 minutes). Then, a paraformaldehyde (PFA) solution (4%, 1 ml) was added and the cells were incubated for 30 minutes and fixed. The cells were washed 3 times with PBS (the same as above). Subsequently, a PBS solution (1 ml) containing triton (0.25%) was added and the cells were incubated at 37° C. for 15 minutes. The cells were washed 3 times with PBS (the same as above). Then, a PBS solution (1 ml) containing BSA (bovine serum albumin, 1%) was added and the cells were incubated at room temperature for 1 hour. Subsequently, the cells were washed 3 times with PBS (the same as above).

A sufficient amount of a primary antibody staining solution (0.1% BSA BSH antibody in PBS [1:200] (final concentration 0.5 μg/ml)) was added to cover samples other than negative control. For the negative control, the same solution used to dilute the antibody which did not contain the primary antibody was used. The samples were incubated respectively at room temperature for 2 hours. The primary antibody staining solution was removed from the sample and subsequently the cells were washed 3 times with PBS (the same as above). A sufficient amount of a secondary antibody staining solution (0.1% BSA donkey anti-mouse IgG (Alexa 488) in PBS [1:100]) was added to cover the sample, which was incubated at room temperature for 2 hours. The same procedure was carried out for negative control which did not contain the secondary antibody. The secondary antibody staining solution was removed from the sample and subsequently the cells were washed 3 times with PBS (the same as above).

A mountant (ProLong (registered trademark) Diamond: Thermo) was added onto a glass preparate to fix the sample. In this way, a cell immunostaining glass preparate of cancer cell U87ΔEGFR was prepared.

(2) Experimental Results

Figure 9:
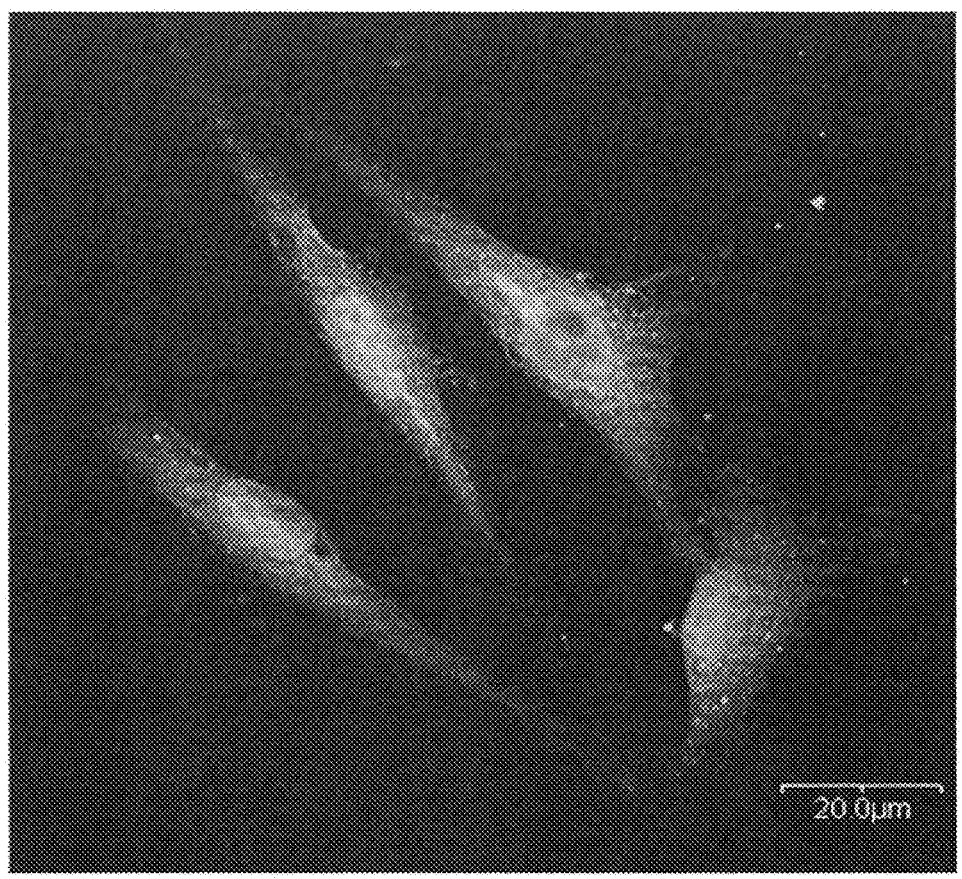
FIG. 9 is an image showing U87ΔEGFR subcellular distribution of BSH contained in a complex obtained by mixing A6K (TFA salt) and BSH in an aqueous solution using a specific antibody recognizing BSH.

A stain image is shown in FIG. 9. The stains were detected not only in the cytoplasm but also in the nucleus, thereby verifying that the complex of the present invention moved not only into the cell but also into the nucleus. From these results, it can be said that by irradiating a neutron beam to a cell containing a complex of the present invention, the cell can be selectively destroyed thereby enabling an efficient cancer therapy.

Example 4

A neutron was irradiated to a cancer cell containing a complex of the present invention to investigate colony formation inhibition.

(1) Production of a Complex Containing A6K (Hydrochloride Salt) and BSH

Figure 10:
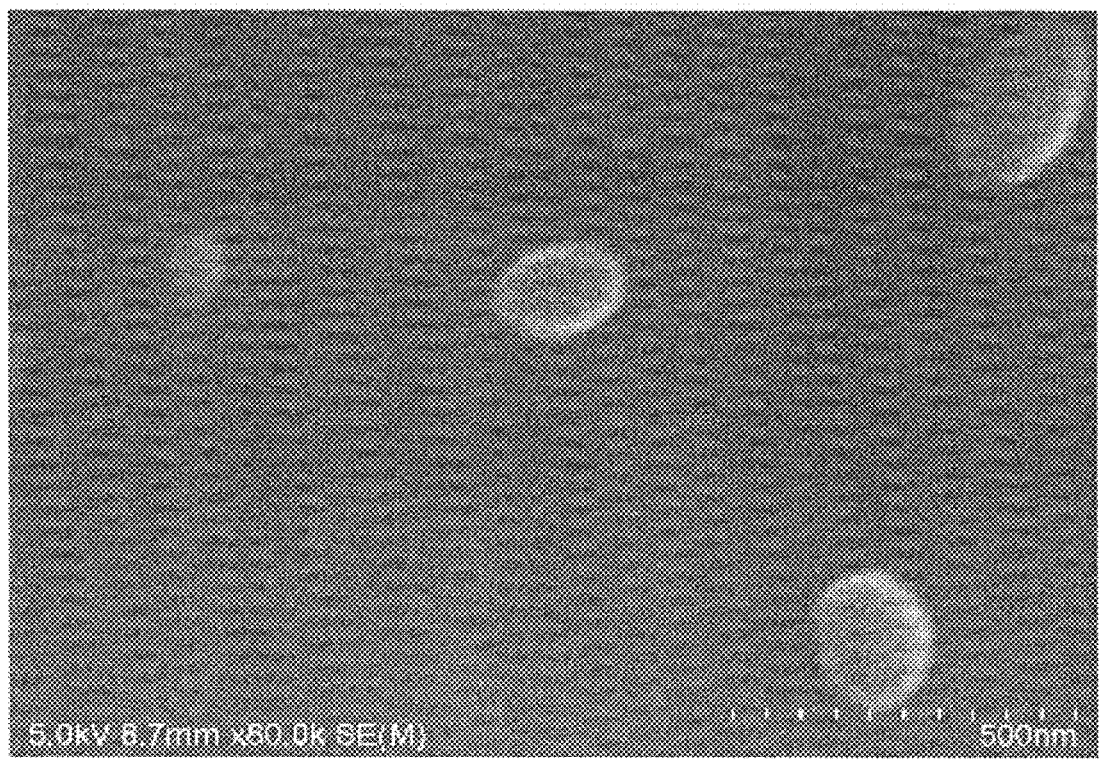
FIG. 10 is a scanning electron micrograph of a complex obtained by mixing A6K (hydrochloride salt) (166 μM) and BSH (1.66 mM) in an aqueous solution. A bar at bottom right is 500 nm.

A lyophilized product of A6K (hydrochloride salt) synthesized by a routine method was dissolved in Milli-Q water and ultrasonication was carried out for 10 minutes. A part of the obtained aqueous solution of A6K (hydrochloride salt) in Milli-Q was separated and observed using a scanning electron microscope and a transmission electron microscope. A6K (hydrochloride salt) had a tubular form. BSH was added to the aqueous solution of A6K (hydrochloride salt) in Milli-Q, mixed with stirring at room temperature for 3 minutes, and subjected to ultrasonication for 10 minutes. A complex in a spherical shape was obtained when molar ratios of A6K (hydrochloride salt) to BSH were 1:10 (166 μM:1.66 mM) and 1:25 (166 μM:4.15 mM). Most of the obtained complex had a diameter of about 100 nm. A scanning electron micrograph of the complex when a molar ratio of A6K (hydrochloride salt) to BSH was 1 to 10 was shown in FIG. 10.

(2) Delivery of a Complex into a Cancer Cell

Figure 11:
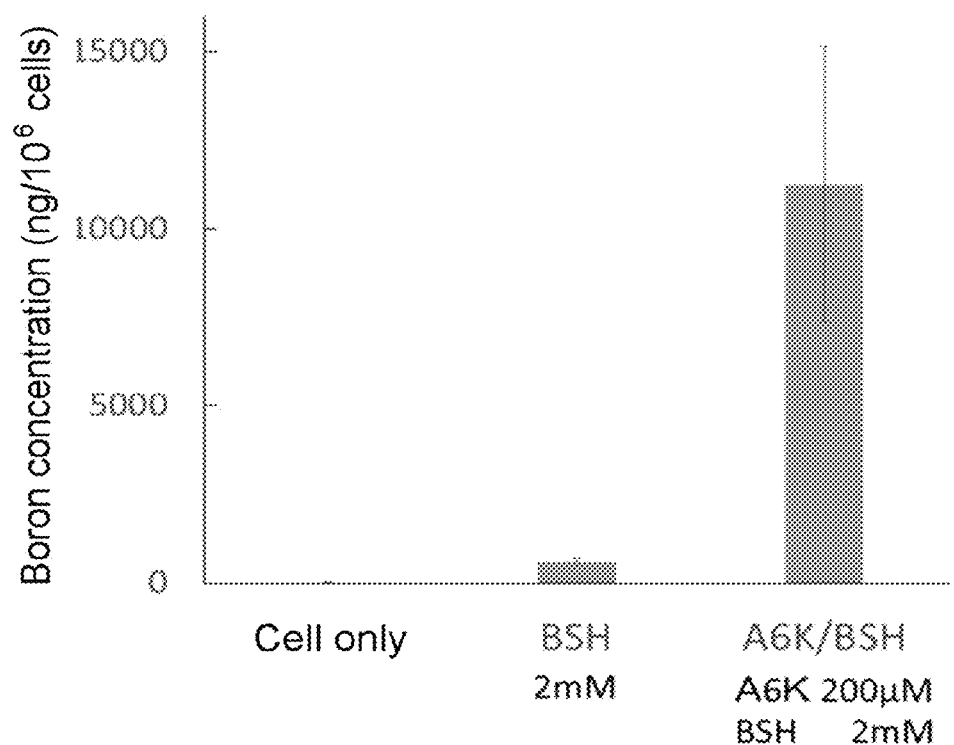
FIG. 11 is a graph showing the cell introduction of a complex obtained by mixing A6K (hydrochloride salt) and BSH in an aqueous solution. An amount of the complex delivered into the cell was investigated using Inductively Coupled Plasma-Atomic Emission Spectroscopy (ICP-AES).

The complex containing A6K (hydrochloride salt) and BSH obtained in the above (1) (a molar ratio of A6K (hydrochloride salt):BSH was 1:10) was added to a glioma cell line U87ΔEGFR in a similar procedure to that described in Example 2 (2). The complex was added in an amount in such a way that final concentrations of A6K (hydrochloride salt) and BSH were as shown in FIG. 11. The cells were incubated with the complex, at 37° C. for 24 hours and subsequently subjected to ICP-AES thereby to measure a boron concentration in the cell. As shown in FIG. 11, the group to which only BSH (2 mM) was added had an intracellular boron concentration of 595.2±105.1 ng/$10^6$ cells, whereas the group to which the complex of A6K (hydrochloride salt) (200 μM) and BSH (2 mM) was added had an intracellular boron concentration of 11262±3890 ng/$10^6$ cells. From these results, it was found that the present complex was specifically taken into a cancer cell and a high concentration of the complex retained in the cell even after 24-hour incubation.

(3) Localization of a Complex in a Cell

Figure 12:
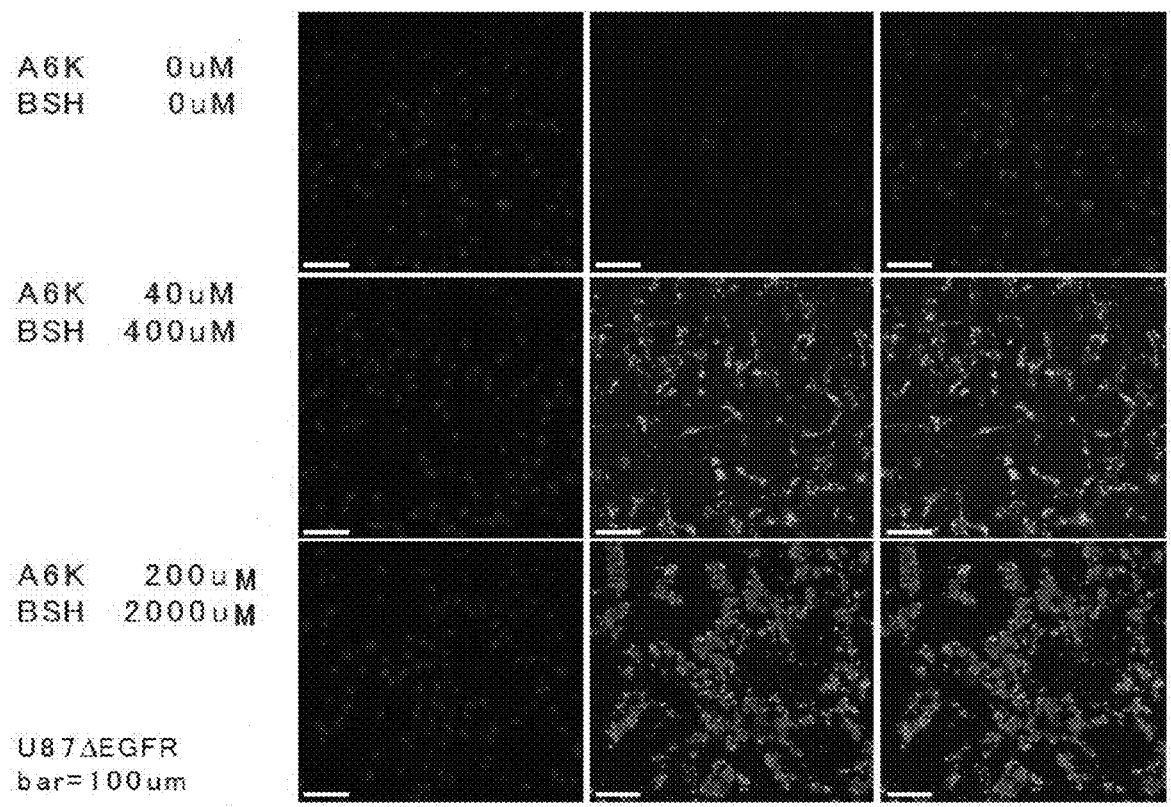
FIG. 12 is an image showing U87ΔEGFR subcellular distribution of BSH contained in a complex obtained by mixing A6K (hydrochloride salt) and BSH in an aqueous solution using a specific antibody recognizing BSH. A left column is nuclear staining images showing the presence of cells. A middle column shows the local presence of BSH by an anti-BSH antibody. The staining images and a right column are images obtained by superposing the left column over the middle column. Numbers at left of the images are mixing ratios of A6K (hydrochloride salt) to BSH. A bar at bottom left in each image is 100 microns.

Subcellular distribution of the complex of A6K (hydrochloride salt) and BSH delivered into a cell was investigated in a similar procedure to that described in Example 3 (1). Micrographs of cancer cells stained using a BSH specific antibody are shown in FIG. 12. From these results, the intracellular introduction of the boron drug BSH was confirmed in both A6K (hydrochloride salt)/BSH complex 40 μM/400 μM administered group and 200 μM/400 μM administered group. It can be said that by irradiating a neutron beam to a cell containing a complex of the present invention, the cell can be selectively destroyed thereby enabling an efficient cancer therapy.

Example 5

A neutron was irradiated to a cancer cell containing a complex of the present invention to carry out a colony formation test.

Figure 13:
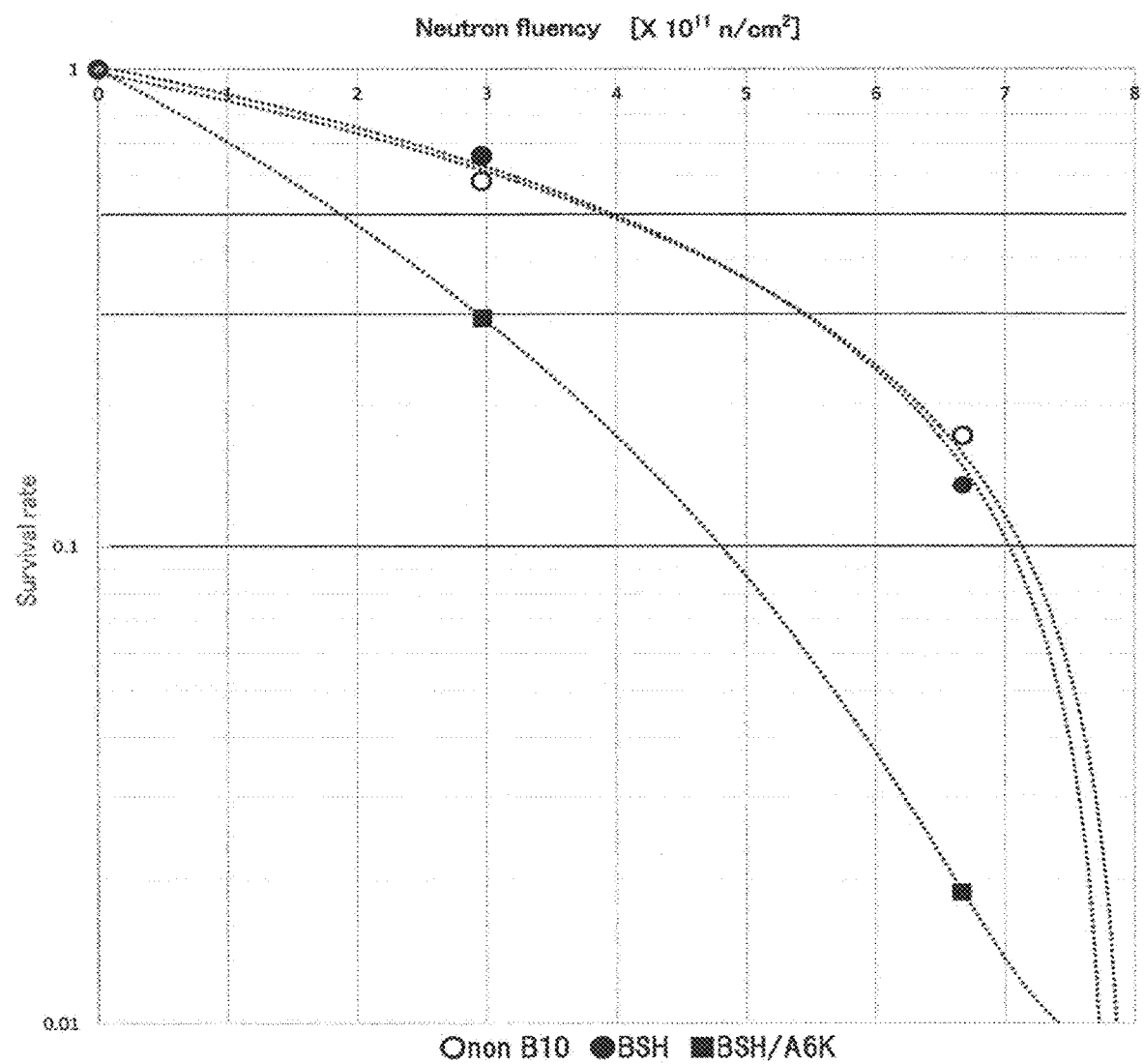
FIG. 13 is a graph showing a survival rate of cancer cells when a neutron beam is irradiated to the cancer cells containing a complex containing A6K (TFA salt) and BSH. non B10 is a system wherein neither the complex or BSH was added to cells, BSH is a system wherein only BSH was added to cells, BSH/A6K is a system wherein the complex containing A6K (TFA salt) and BSH was added to cells.

The complex containing A6K (hydrochloride salt) and BSH obtained in Example 4 (1) was added to a tongue squamous cell carcinoma-derived cell line (SAS) in a similar procedure to that described in Example 2 (2). The complex was added in an amount in such a way that A6K (hydrochloride salt) was 20 μM and BSH was 2000 μM (0.24 mg/ml as B10). The test was carried out on the system to which only BSH (2000 μM) was added (0.24 mg/ml as B10) and the system to which neither the complex or BSH was added. Both systems were incubated at 37° C. for 24 hours. Neuron beam irradiation was carried out for 20 minutes, 45 minutes, and 90 minutes. A survival rate of the cell was calculated by the colony formation method. In each system, the number of samples (N) was 3. The results are shown in FIG. 13. It was confirmed that the survival rate of cancer cells containing the complex containing A6K (hydrochloride salt) and BSH notably decreased as neutron fluency increased. When neutron fluency was $6.7 \times 10^{11}$ n/$cm^2$, the survival rate of cancer cells containing neither the complex nor BSH, and the survival rate of cancer cells containing only BSH were 10 to 20%, whereas the survival rate of cancer cells containing the above complex was only 2% or less. From these results, it was shown that when a cell containing a complex of the present invention is irradiated with a neutron beam, such a cell can be selectively destroyed thereby verifying that an efficient cancer therapy was enabled.

Example 6

A drug of the present invention was administered to a brain tumor model animal (in vivo model into which U87ΔEGFR was transplanted) to investigate whether or not BSH was tumor-specifically introduced.

Animals used in the present experiment were bred, housed and used in accordance with the procedure approved (approval code: OKU-2016475) by the Animal Care and Use Committee, Okayama University. Tumor-bearing model mice (BALB/C nu/nu, female, 6 to 8 weeks of age, 25 g, Japan SLC, Inc., Shizuoka) were created by directly injecting 3 μL of a U87ΔEGFR cell suspension ($1 \times 10^5$ cells/μL) into the brain. Two weeks later, 200 μL of the complex containing A6K and BSH (A6K 2 mM/BSH 20 mM) and 200 μL of BSH 20 mM as control experiments were respectively administered from the tail vein (given that a mouse body weight was 20 g, A6K.HCl was converted to 8 mg/kg and BSH was converted to 33.4 mg/kg.)

The complex used in the experiment (the compound described in Example 4 (1)) was prepared as follows. 70 μL of MQ water was added to 70 μL of A6K 10 mM to adjust to A6K 5 mM. 35 μL of BSH 200 mM and 175 μL of MQ water were added to 140 μL of A6K 5 mM to prepare a solution of A6K 2 mM/BSH 20 mM. A6K was obtained from 3-D Matrix, Ltd. and BSH was obtained from STELLA PHARMA CORPORATION.

Twelve hours after administration, the mouse brain was embedded using an embedding medium for a frozen tissue section, tissue tek O.C.T compound. The brain, after frozen, was thinly sliced to a thickness of 10 μm to create a frozen section. The frozen section was fixed at room temperature for 10 minutes using 4% (w/v) paraformaldehyde (PFA, Wako Pure Chemical Corporation). After washing with PBS, the section was blocked with 1% (w/v) BSA and immersed in a solution of anti-BSH mouse monoclonal antibody containing 0.3% (v/v) TritonX-100 (5 μg/mL) and rabbit anti-HLA-A antibody for 2 hours at room temperature. After washing, the section was immersed for 2 hours at room temperature in a solution of a donkey anti-mouse antibody (Life Technologies) labelled with Alexa-Fluor 488 (green fluorescence) (20 μg/mL) and a solution of a goat anti-rabbit antibody (Life Technologies) labelled with Alexa-Fluor 555 (red fluorescence) (2 μg/mL). After washing, the nucleus was stained with Hoechst 33258 to create a preparate, which was subsequently observed for the local presence of BSH using a confocal laser microscope. The anti-BSH antibody, provided by Professor Kirihata of Osaka Prefecture University, diluted and frozen, was thawed when used.

HLA-A is a human major histocompatibility antigen and expressed in transplanted and proliferated human-derived malignant glioblastoma U87ΔEGFR while it is not expressed in normal brain tissues of a mouse. In the present experiment, HLA-A was detected with red fluorescence. It was confirmed, because there were cell populations having red fluorescence and boundaries were clear, that the human-derived malignant glioblastoma U87ΔEGFR proliferated in the brain of a nude mouse whereby a human brain tumor model was created.

Figure 14:
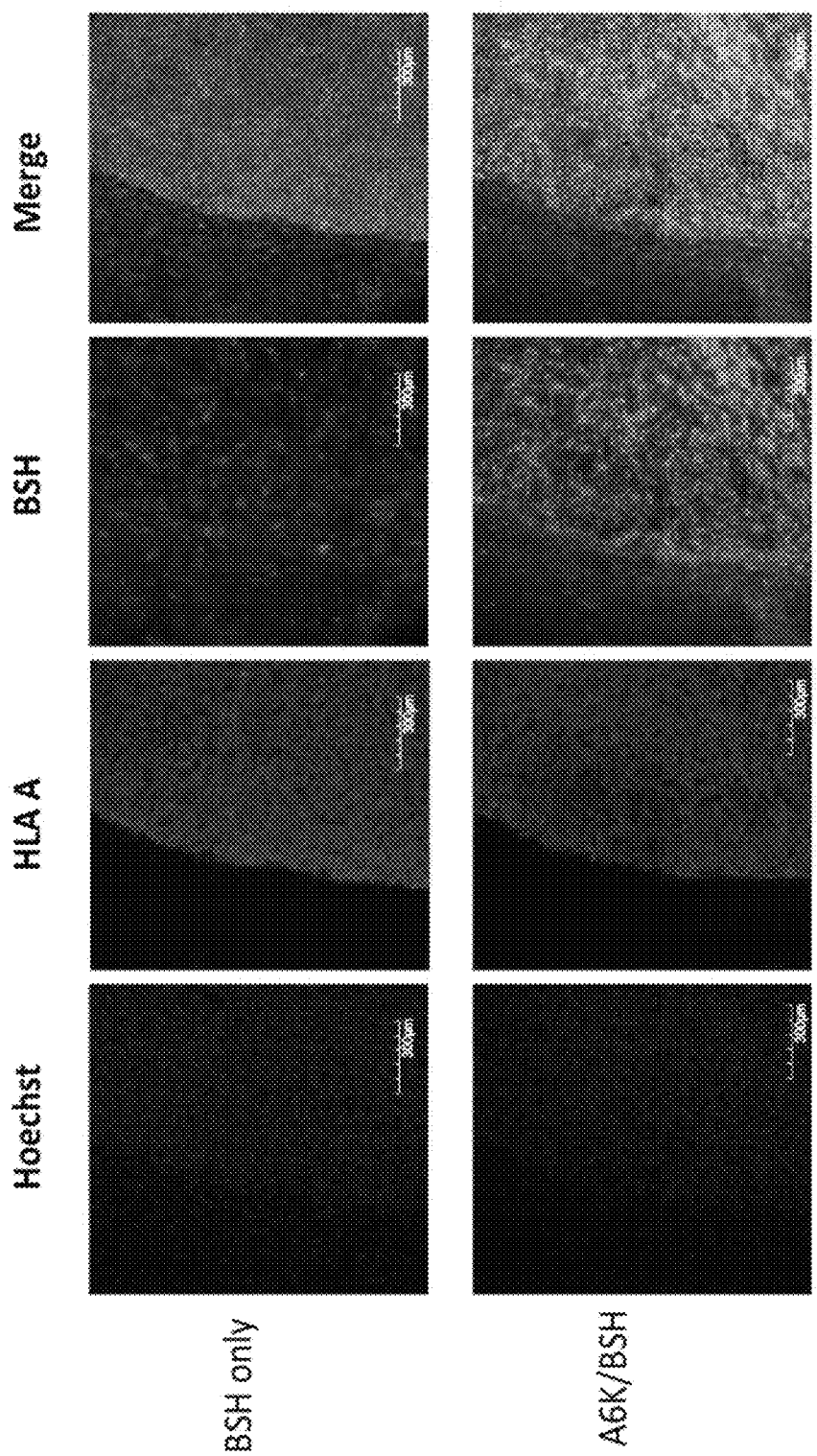
FIG. 14 is images showing BSH being introduced into tumor site-specifically by a drug of the present invention. Upper images (indicated as BSH only) show the cases where only BSH was administered, and lower images (A6K/BSH (the compound described in Example 4 (1)) show tumor tissues when a drug (a complex containing A6K and BSH) of the present invention was administered thereto. Hoechst shows nuclear staining images, HLA-A shows immunostaining images of HLA-A, BSH shows immunostaining images of BSH, and Merge shows images obtained by merging these three layers of staining on the same screen.

The compound (A6K/BSH) described in Example 4 (1) was administered once to these brain tumor model animals from the tail vein, and the brain tumor tissue was removed after 12 hours, immunohistostained using an anti-BSH mouse monoclone antibody, and detected for the presence of BSH using green fluorescence. For a control experiment, BSH in the same amount was administered singly. Summary of the results is shown FIG. 14.

Intense green color indicating the presence of BSH was detected in the mouse to which the compound described in Example 4 (1) (A6K/BSH) was administered, and further the green color corresponded with the tumor tissue which was HLA-A positive (red). The green color was weak in the control experiment in which only BSH was administered, thereby it was confirmed that BSH was not much taken into the cells and that the locations where BSH was present were not different between tumor tissues and normal brain tissues of the mouse.

In the present experiment, human-derived glioblastoma was transplanted into a nude mouse brain to create a brain tumor model animal, and it was confirmed that BSH could be brain tumor site-specifically introduced by the administration of the compound described in Example 4 (1).

INDUSTRIAL APPLICABILITY

The present invention can be used for producing a cancer therapy drug, particularly in the field of radiotherapy drugs of cancer.

---

The invention claimed is:

1. A complex, comprising a peptide comprising a repeating hydrophobic amino acid residue and a basic amino acid residue and BSH, wherein the complex is in a spherical shape having a diameter of about 20 nm to about 200 nm.

2. The complex of claim 1, wherein the peptide is represented by the following formula (1):

$$(X)_m - (Z)_n \quad (1)$$

wherein m represents a number of amino acid residues X that are each independently alanine, valine, leucine, or glycine; n represents a number of amino acid residues Z that are each independently —NHCH(COOH)$R^1$; $R^1$ is —(CH$_2$)$_p$NHR$^2$; $R^2$ is —H or —C(NH)NH$_2$; m is 4 to 10; n is 1 to 2; and p is 1 to 6.

3. The complex of claim 2, wherein X is alanine; m is 6; Z is lysine, arginine, homoarginine, ornithine, 2,7-diaminoheptanoic acid, 2,4-diaminobutyric acid, or 2-amino-4-guanidinobutyric acid; and n is 1.

4. The complex of claim 3, wherein X is alanine; m is 6; Z is lysine or arginine; and n is 1.

5. A composition, comprising the complex of claim 1 and a pharmaceutically acceptable carrier or excipient.

6. A method for treating glioma, head cancer and neck cancer, the method comprising administering the complex of claim 1 to a cancer patient and irradiating the cancer patient with a neutron beam.

7. The composition of claim 5, wherein X is Marline; m is 6; Z is lysine or arginine; and n is 1 in the peptide.

8. The method of claim 6, wherein X is alanine; in is 6; Z is lysine or arginine; and n is 1 in the peptide.

9. The composition of claim 5, which is in the form of an intravenous injection or an infusion.

10. The method of claim 6, wherein the complex is administered by intravenous injection or infusion.

* * * * *